(12) United States Patent
Qiao et al.

(10) Patent No.: US 12,109,285 B2
(45) Date of Patent: *Oct. 8, 2024

(54) ZINC PHOSPHATE COMPLEX FOR ORAL CARE

(71) Applicant: Colgate-Palmolive Company, New York, NY (US)

(72) Inventors: Baohua Qiao, Howell, NJ (US); Long Pan, Somerset, NJ (US); Gregory Szewczyk, Flemington, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/539,748

(22) PCT Filed: Dec. 26, 2014

(86) PCT No.: PCT/US2014/072423
§ 371 (c)(1),
(2) Date: Jun. 26, 2017

(87) PCT Pub. No.: WO2016/105432
PCT Pub. Date: Jun. 30, 2016

(65) Prior Publication Data
US 2017/0348207 A1    Dec. 7, 2017

(51) Int. Cl.
| | |
|---|---|
| *A61K 8/27* | (2006.01) |
| *A61K 6/20* | (2020.01) |
| *A61K 6/74* | (2020.01) |
| *A61K 8/24* | (2006.01) |
| *A61K 33/42* | (2006.01) |
| *A61Q 11/00* | (2006.01) |

(52) U.S. Cl.
CPC ............ *A61K 8/27* (2013.01); *A61K 6/20* (2020.01); *A61K 6/74* (2020.01); *A61K 8/24* (2013.01); *A61K 33/42* (2013.01); *A61Q 11/00* (2013.01); *A61K 2800/58* (2013.01)

(58) Field of Classification Search
CPC ... A61K 8/27; A61K 6/20; A61K 6/74; A61K 8/24; A61K 33/42; A61K 2800/58; A61Q 11/00
See application file for complete search history.

(56) References Cited

U.S. PATENT DOCUMENTS

| | | | |
|---|---|---|---|
| 4,894,220 A | 1/1990 | Nabi et al. | |
| 5,000,944 A | 3/1991 | Prencipe et al. | |
| 5,378,401 A * | 1/1995 | Derham | C01B 25/40 252/387 |
| 6,984,376 B2 | 1/2006 | Stephenson et al. | |
| 8,906,347 B2 | 12/2014 | Strand et al. | |
| 2003/0138384 A1 | 7/2003 | Stephenson et al. | |
| 2006/0099152 A1 | 5/2006 | Day et al. | |
| 2007/0025928 A1 | 2/2007 | Glandorf et al. | |
| 2011/0076309 A1 | 3/2011 | Misner et al. | |
| 2017/0326046 A1 | 11/2017 | Pan et al. | |
| 2017/0340533 A1 | 11/2017 | Qiao et al. | |
| 2017/0340534 A1 | 11/2017 | Nawrocki et al. | |
| 2017/0348352 A1 | 12/2017 | Qiao et al. | |
| 2018/0008519 A1 | 1/2018 | Qiao et al. | |

FOREIGN PATENT DOCUMENTS

| | | |
|---|---|---|
| CN | 101330900 A | 12/2008 |
| CN | 101384266 A | 3/2009 |
| CN | 103648471 A | 3/2014 |
| WO | WO 1994/014406 | 7/1994 |
| WO | WO 2001/039606 | 6/2001 |
| WO | WO 2002/092038 | 11/2002 |
| WO | WO 2013/013903 | 1/2013 |

OTHER PUBLICATIONS

Sigma-Aldrich, sodium hexametaphosphate product page. accessed Jun. 23, 2019 (Year: 2019).*
ICL Performance Products LP, 2005, "Hexaphos™ Sodium Hexametaphosphate (SHMP) Plates Product Data Sheet," http://www.alchemical.com/products.html?file=tl_files/product_documents/MSDS/ICL/SHMP_Hexaphos_Plates-Tech_Data-11-05-05.pdf.
International Search Report and Written Opinion of the International Searching Authority in International Application No. PCT/US2014/072423, dated Aug. 27, 2015.
Momeni et al., 2014, "Comprehensive Study of the Chelation and Coacervation of Alkaline Earth Metals in the Presence of Sodium Polyphosphate Solution," Langmuir 30(18):5256-5266.
Rashchi et al., 2000, "Polyphosphates: A Review of Their Chemistry and Application with Particular Reference to Mineral Processing," Minerals Engineering 13(10-11):1019-1035.
Lanigan, R., "Final report on the safety assessment of Sodium Metaphosphate, Sodium Trimetaphosphate, and Sodium Hexametaphosphate," International Journal of Toxicology. 20 Suppl 3:75-89 (2001)(abstract only).

* cited by examiner

*Primary Examiner* — Adam C Milligan

(57) ABSTRACT

An oral care composition having a soluble zinc polyphosphate complex made by combining ingredients including an inorganic zinc salt, and a plurality of long chain polyphosphates having 6 or more phosphate polymer units, the relative amount of inorganic zinc salt and long chain polyphosphates providing a phosphorus to zinc mole ratio of at least 6:1. Further provided is a method of treating a subject suffering from dentinal sensitivity applying the oral care composition to the teeth and gums of the subject.

3 Claims, No Drawings

ZINC PHOSPHATE COMPLEX FOR ORAL CARE

BACKGROUND

The present disclosure is directed to a soluble zinc polyphosphate complex for use in personal care compositions and methods of making the complex.

Zinc compounds are often used in oral care and personal care compositions. For instance, zinc is known for use in oral care products as an anti-plaque agent. Compounds such as zinc citrate and zinc oxide have been applied to toothpaste to prevent plaque buildup. Zinc salts can also have other functions related to the body, such as antimicrobial and/or anti-inflammatory effects, which can make them desirable as active ingredients in personal care products including antiperspirants and deodorants, among others.

Polyphosphates are also known in the art for use as, for example, chelants, in oral care compositions. In addition, polyphosphates such as diphosphate (also known as pyrophosphate) and triphosphate are known for use as anions in antiperspirants, as taught in WO 2013/013903, published on Jan. 31, 2013. Longer chain linear polyphosphates (more than 3 phosphate units) are susceptible to hydrolysis in aqueous compositions. Upon hydrolysis they are known to form orthophosphates which form insoluble zinc complexes.

Dentinal hypersensitivity (i.e. sensitivity) is a painful condition resulting from the movement of liquid in exposed dentin tubules from external stimuli such as pressure and temperature. One strategy to reduce and or eliminate the pain resulting from exposed dentin tubules is to form insoluble precipitates in the tubules in order to physically plug the tubules. For instance, Stannous salts have been shown to treat dentinal hypersensitivity by depositing into tubules from neat solutions and from simple formulations, as described in U.S. Patent Application Publication No. 2009/0136432, the disclosure of which is hereby incorporated by reference in its entirety.

Antiperspirant substances often employ aluminum containing actives. These substances reduce the flow of sweat by forming a plug in the sweat duct. However, due to consumer concern about aluminum based antiperspirant products, Aluminum free antiperspirant actives are in demand.

The discovery of a novel zinc complex that can be used to treat dentinal hypersensitivity and/or that can act as an active in other personal care products, such as antiperspirants or deodorants, would be a welcome addition to the art.

BRIEF SUMMARY

An embodiment of the present disclosure is directed to an oral care composition, comprising: a soluble zinc polyphosphate complex made by combining ingredients comprising an inorganic zinc salt, and a plurality of long chain polyphosphates having 6 or more phosphate polymer units; wherein the relative amount of inorganic zinc salt and long chain polyphosphates provides a phosphorus to zinc mole ratio of at least 6:1.

In another embodiment, the present disclosure is directed to a method of treating a subject suffering from dentinal hypersensitivity, the method comprising: providing an oral care composition comprising a soluble zinc polyphosphate complex made by combining ingredients comprising an inorganic zinc salt, a plurality of long chain polyphosphates having 6 or more phosphate polymer units, and a solvent; and applying the oral care composition to the teeth and gums of the subject in an amount that is efficacious for treating dentinal hypersensitivity; wherein the relative amount of inorganic zinc salt and long chain polyphosphates provides a phosphorus to zinc mole ratio of at least 6:1.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An embodiment of the present disclosure is directed to a soluble zinc polyphosphate complex. The complex is made by combining ingredients comprising an inorganic zinc salt, a plurality of long chain polyphosphates having 6 or more phosphate polymer units and an aqueous solvent. The relative amount of inorganic zinc salt and long chain polyphosphates provides a phosphorus to zinc mole ratio of at least 6:1, such as about 15:1 to about 25:1.

In one embodiment, the zinc polyphosphate complex has the property of reduced solubility in water at a first condition of 37° C. and a pH of about 7.4 in the presence of 1% by weight Bovine Serum Albumin protein when compared with a second condition of 25° C. and a pH below 5.5, such as 5.4, in the absence of protein. The reduction in solubility is sufficient to allow a desired amount of the soluble zinc polyphosphate complex in a saturated solution at the second condition to precipitate from the saturated solution at the first condition.

The complex can be made using any suitable inorganic zinc ion source. Examples of suitable inorganic zinc salts include zinc chloride, zinc oxide, zinc sulfate, zinc carbonate, zinc fluoride, zinc peroxide, zinc phosphate, zinc pyrophosphate, zinc silicate and combinations thereof.

Any polyphosphates having for more phosphate polymer units can be employed. In an embodiment, long chain polyphosphate having about 6 to about 50 phosphate polymer units, such as about 6 to about 30 phosphate polymer units, can be used. An example of a long chain polyphosphate is sodium hexametaphosphate ("SHMP").

The phosphorus to zinc ratio can be any ratio that results in a soluble complex at the desired pH in an aqueous solution. In an embodiment, the phosphorus to zinc mole ratio ranges from about 6:1 or more, such as about 10:1 to about 55:1, such as about 12:1 to about 40:1, or about 15:1 to about 25:1 or about 18:1 to about 23:1 or about 20:1 to about 23:1. The amount of zinc ion source to phosphate polymer reactant employed will vary depending on the desired phosphorus to zinc ratio and the particular reactants used.

In an embodiment, the resulting zinc polyphosphate complex has an average of 15 or more P atoms. For example, the zinc polyphosphate complex can have an average of about 18 to about 25 P atoms, or about 20 to about 23 P atoms. For a zinc polyphosphate complex with a ratio of P:Zn of about 21:1, it can be predicted that approximately 1 zinc is bound to each phosphate chain on average.

In an embodiment, the zinc polyphosphate complex has a property of becoming insoluble in aqueous solution at a pH ranging from above 5.5, such as about 6 or about 6.2 to about 6.5. The zinc polyphosphate complex can also have the property of being insoluble at a below 6 in aqueous solution in the presence of salivary proteins.

Oral Care Compositions

When used in an oral care product, the soluble zinc and polyphosphate complexes of the present disclosure can remain soluble in composition until introduced into the oral cavity of a patient, at which point the complexes precipitate on biomaterial surfaces such as dentinal tubules. For example, the soluble zinc polyphosphate complex can diffuse into dentinal tubules and precipitate, to thereby physically occlude the dentinal tubules and prevent dentinal hypersensitivity. In addition, as long as protein, such as BSA is involved, which may come from saliva, the zinc precipitate can have relatively strong acid resistance. Based on these properties, the novel zinc complexes of the present disclosure are potential candidates for, among other things, toothpastes for dentinal hypersensitivity relief.

The zinc polyphosphate complexes of the present disclosure can have one or more of the following advantages: the ability to remain soluble at a pH of 6.1 or less, such as about 5.5 or less; the ability to precipitate at a pH above 5.5, such as about 6.2 or more, the ability to occlude dentin tubules and relieve or eliminate dentinal hypersensitivity; and/or the ability to form precipitates that remain insoluble at a pH below 6 in the presence of salivary proteins; the ability to in situ generate a precipitate upon interaction with saliva to effectively deliver zinc to the oral surface and provide dentin sensitivity relief, antimicrobial function, or any other benefit that may become apparent; the ability to in situ generate a precipitate upon interaction with skin proteins; or the ability to provide antimicrobial and/or anti-inflammatory effects when applied in a personal care product other than oral care products, such as deodorants, or antiperspirants. Thus, this complex has high potential in the oral care and personal care fields.

The present disclosure is also directed to a method of making a soluble zinc polyphosphate complex. The method comprises combining inorganic zinc salt; a plurality of long chain polyphosphates having 6 or more phosphate polymer units; and a solvent. As discussed above, the relative amount of inorganic zinc salt and long chain polyphosphates provides a phosphorus to zinc mole ratio of at least 6:1. The ingredients can be mixed in any suitable order and using any suitable mixing technique with or without heating, so long as the method results in the formation of the desired soluble zinc polyphosphate complex.

In certain embodiments, the solvent used in the method is at least one solvent chosen from water, glycerin, diglycerol (glycerol-2), triglycerol (glycerol-3), quadraglycerol (glycerol-4), sorbitol, and polyethylene glycol having a weight average molecular weight less than 10,000. In one embodiment, the solvent is water. In one embodiment, the amount of solvent is 40 to 90 weight % based on a total weight of inorganic zinc salt, polyphosphate, and solvent. In other embodiments, the amount of solvent is 70 to 90 weight %, 75 to 85 weight %, or about 80 weight %.

The present disclosure is also directed to an oral care composition. The composition comprises a soluble zinc polyphosphate complex made by combining ingredients comprising an inorganic zinc salt, a plurality of long chain polyphosphates having 6 or more phosphate polymer units, and an aqueous solvent. The relative amount of inorganic zinc salt and long chain polyphosphates provides a phosphorus to zinc mole ratio of at least 6:1, as described herein above.

The target amount of zinc to precipitate in the oral care composition can be any amount that will reduce dentinal hypersensitivity to a desired degree. In an embodiment, the amount is about 0.1 or more, such as about 0.1 to about 0.5, or about 0.3 to about 0.4. Suitable amounts of soluble zinc complex can be provided in the oral composition to achieve the desired target precipitate during use.

The oral compositions may be provided in an orally acceptable carrier or vehicle. The carrier can be a liquid, semi-solid, or solid phase, in the form of a mouthrinse, dentifrice (including toothpastes, toothpowders, and prophylaxis pastes), confectionaries (including lozenges and gum), medicament, film, or any other form known to one of skill in the art. Selection of specific carrier components is dependent on the desired product form.

In various embodiments, the oral composition has an orally acceptable vehicle that has a pH of about 5.5 to about 10, or about 5.8 or 6 to 6.1, 7 or 9. Certain components serve to raise the pH of the oral composition. Such compounds include conventional buffers and salts, as well as chemicals such as the anionic linear polycarboxylates (described above) and polyacrylates such as those available from B.F. Goodrich of Cleveland, Ohio and sold under the trade name CARBOPOL® have been observed to raise pH when present in oral compositions.

Conventional ingredients can be used to form the carriers listed above. The oral compositions may include other materials in addition to those components previously described, including for example, surface active agents, such as surfactants, emulsifiers, and foam modulators, viscosity modifiers and thickeners, humectants, diluents, additional pH modifying agents, emollients, moisturizers, mouth feel agents, sweetening agents, flavor agents, colorants, preservatives, solvents, such as water and combinations thereof. Any given material may serve multiple purposes within two or more of such categories of materials. Preferably, such carrier materials are selected for compatibility and stability with all of the constituents of the active ingredient.

Useful surface active agents are known in the art, such as those disclosed in U.S. Pat. No. 4,894,220, the disclosure of which is incorporated herein by reference in its entirety. Surface active agents can function as surfactants, emulsifiers foam modulators, and/or active ingredient dispersion agents.

Suitable surface active agents are those that are reasonably stable and foam throughout a wide pH range. These compounds are known in the art, and include non-soap anionic (e.g., sodium lauryl sulfate (SLS), N-myrstoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan monooleate, TWEEN® 80), Poloxamer 407, available under the trade name PLURONIC® F127 from BASF Corporation), cationic, zwitterionic (e.g., cocoamidopropyl betaine and lauramido propyl betaine), and amphoteric organic synthetic detergents. In various embodiments, one or more surface active agents are present in the oral composition in the range of about 0.001% to about 5%, or about 0.5% to about 2.5%. In embodiments where the oral composition comprises an active ingredient comprising lipophilic active compound(s), the amount of surface active agent can be increased to enable sufficient emulsification of the active ingredients within the carrier of the oral composition. The carrier can be, for example, an aqueous carrier.

In an embodiment, the zinc salts can be used in translucent aqueous formulations, such as mouthrinse. In embodiments where the oral composition is in the form of a mouthrinse an exemplary carrier is substantially liquid. The term "mouthrinse" includes mouthwashes, sprays and the like. In such a preparation the orally acceptable carrier typically has an aqueous phase comprising either water, or a water and alcohol mixture. Further, in various embodiments, the oral carrier can comprise, for example, a humectant, surfactant, and a pH buffering agent.

The oral composition may optionally comprise a flavoring agent. Exemplary flavoring substances are known to a skilled artisan, and may be present in certain embodiments at a concentration of about 0.05% by weight to about 5% by weight.

In embodiments where an oral composition is in the form of a confectionary, an exemplary carrier may be substantially solid or semi-solid. Confectionary carriers are known in the art. For a lozenge, the carrier can comprise, for example, a lozenge base material (for example, comprising a non-cariogenic polyol and/or starch/sugar derivative), an emulsifier, a lubricant, a flavoring agent, a thickener, and optionally a coating material. Chewing gum carriers generally have a chewing gum base, one or more plasticizing agents, a sweetening agent, and a flavoring agent.

In embodiments where an oral composition is in the form of a film, an exemplary carrier is substantially solid or semi-solid. Such film carriers can comprise, for example, a water soluble or dispersible film forming agent, such as a hydrophilic polymer. Optionally, the film carrier may also comprise hydrophobic film forming polymers, either as a removable backing layer, or mixed with a hydrophilic film forming polymer. Film carriers optionally comprise plasticizers, surface active agents, fillers, bulking agents, and viscosity modifying agents.

In embodiments where an oral composition is in the form of a dentifrice, an exemplary carrier is substantially semi-solid or a solid. Dentifrices can comprise, for example, surface active agents, humectants, viscosity modifying agents and/or thickeners, abrasives, solvents, such as water, flavoring agents, and sweetening agents. In an embodiment, the dentifrice is a toothpaste.

In embodiments an oral composition is in the form of a medicament, such as a non-abrasive gel or ointment that can be applied to the gingival sulcus or margin and can be used in conjunction with wound dressings, gauze, films, and the like. Such gels may include both aqueous and non-aqueous gels. Aqueous gels generally comprise a polymer base, a thickener, a humectant, a flavoring agent, a sweetening agent, and a solvent, typically including water.

In various embodiments, the compositions and methods of the present disclosure promote oral health in an oral cavity and treat plaque on an oral surface of a mammalian subject. In one embodiment, a method of providing one or more oral health benefits to an oral cavity of a mammalian subject entails preparing an oral composition as described herein, where an active ingredient comprises any of the soluble zinc polyphosphate complexes disclosed herein. The prepared oral composition is contacted with an oral surface within an oral cavity. In addition to treating dentinal hypersensitivity, the oral composition containing the active ingredient may provide multiple oral health benefits, such as anti-gingivitis, anti-periodontitis, anti-caries, anti-tartar, anti-inflammatory, analgesic, anti-aging, and breath freshening.

Thus, any of the various embodiments of the oral care composition described above are contacted with or applied regularly to an oral surface, such as at least one time a day, or on multiple days in a week.

The oral composition of the present disclosure can be made by any of the methods known in the art for combining ingredients to make oral care compositions. Methods for making the oral compositions comprising a soluble zinc polyphosphate complex, as described herein, are well within the ordinary skill of the art.

Personal Care Compositions

The compositions of the present disclosure can be included in a personal care composition. Examples of such compositions include, but are not limited to, antiperspirants, deodorants, body washes, shower gels, bar soaps, shampoo, hair conditioners and cosmetics.

For antiperspirant and/or deodorant compositions, the carrier can be any carrier that is used for antiperspirants and/or deodorants. The carrier can be in the form of a stick, a gel, a roll-on, or an aerosol. For stick formulations, the carrier may include oils and/or silicones and gelling agents. An example of a formulation can be found in US2011/0076309A1, which is incorporated herein by reference in its entirety.

In an embodiment, the personal care compositions, such as antiperspirants and/or deodorants, include a soluble zinc polyphosphate complex made by combining ingredients comprising an inorganic zinc salt, a plurality of long chain polyphosphates having 6 or more phosphate polymer units, and an aqueous solvent. The relative amount of inorganic zinc salt and long chain polyphosphates provides a phosphorus to zinc mole ratio is at least 6:1, such as at least 15:1, or at least 18:1, such as about 20:1; and can be any of the other phosphorus to zinc mole ratios taught herein for the soluble zinc polyphosphate complex.

The amount of zinc in a personal care composition can be any suitable effective amount. Suitable amounts of zinc can range, for example, from about 0.2% by weight or more, such as about 0.5% to about 10% by weight, relative to the total weight of the composition.

As described above, the zinc polyphosphate complex has the property of reduced solubility in water at certain temperature and pH conditions, but is soluble at other conditions. In an embodiment, the formulation can be formulated without added protein, such as BSA. The protein desired to trigger precipitation can be provided by the sweat of the user after application of the product.

In an embodiment, the zinc polyphosphate complex can have reduced solubility at, for example, a condition of 37° C. and a pH of about 7.4 in the presence of 1% by weight Bovine Serum Albumin protein when compared with a second condition of 25° C. and a pH below 5.5 in the absence of protein. The reduction in solubility can be sufficient to allow a desired amount of the soluble zinc polyphosphate complex in a saturated solution at the second condition to precipitate from the saturated solution at the first condition, as described above.

In an embodiment, the protein can also be used to enhance the efficacy of other antiperspirant salts comprising a polyvalent cation, for example antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine. In an embodiment, these other antiperspirant salts can be added to the formulations of the present disclosure in addition to the zinc polyphosphate complex antiperspirant. In an alternative embodiment, the formulation includes only very small amounts or is entirely or substantially free of the above aluminum or zirconium antiperspirant active complexes. For example, the formulations can include less than 2 wt %, or less than 0.5 wt %, or less than 0.1 wt. %, or less than 0.01 wt. %, or less than 0.001 wt. % or less than 0.0001 wt. % aluminum or zirconium, relative to the total weight of the formulation.

The present disclosure provides antiperspirant products comprising a zinc polyphosphate complex antiperspirant active, e.g., any of the zinc polyphosphate complexes discussed herein, as well as methods of making and using such products. The present disclosure further provides methods of reducing sweat comprising applying the composition to skin, and methods of killing bacteria comprising contacting the bacteria with the composition.

Optional ingredients that can be included in an antiperspirant and/or deodorant formulation of the compositions of the present disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the soluble zinc polyphosphate complex can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition comprising the zinc complexes of the present disclosure. In embodiments, other additives for killing bacteria can also be employed in the compositions. Various suitable additional antimicrobial additives are known in the art.

Thus the present disclosure provides (i) a method for controlling perspiration comprising applying to skin an antiperspirant effective amount of a formulation of any embodiment embraced or specifically described herein; and (ii) a method for controlling odor from perspiration comprises applying to skin a deodorant effective amount of a formulation of any embodiment embraced or specifically described herein.

The present invention is further illustrated through the following non-limiting example(s).

EXAMPLES

Examples 1 to 4

Soluble zinc polyphosphate complex was made by combining 1.277 grams of $ZnCl_2$, 20.972 grams of SHMP and 82.906 grams of water in a batch solution. Four samples were made from the batch solution, which are numbered as examples 1 to 4 in Table 2.

TABLE 2

| Example No. | ZnCl2 + SHMP solution (g) | BSA (g) |
|---|---|---|
| 1. (pH control) | 5 | 0 |
| 2. (pH raised) | 5 | 0 |
| 3. (1% BSA, 37° C.) | 4.6769 | 0.0471 |
| 4. (1% BSA, RT) | 3.874 | 0.039 |

The pH of Example 2 was carefully adjusted from a pH of 4.1 to a pH of 6.2 using dilute NaOH, at which point precipitate formed. However when the precipitated Example 2 had its pH lowered from 6.2 to 5.13 by adding HCl, the precipitates dissolved and the sample became clear again.

BSA protein was added to the formulations of Examples 3 and 4. White precipitate formed immediately in both. Example 3 was then aged at 37° C. for 1 hour. Example 4 was aged at room temperature for 1 hour. Precipitate increased in both example formulations with aging. Based on the color of the solutions, the precipitate increased more in the heated Example 3. The formation of the precipitate indicates that the zinc polyphosphate made using the zinc chloride and SHMP would be suitable for treating dentinal hypersensitivity.

Example 5

The acid resistance of the precipitates was tested by adding dilute HCL to the Example 3 formulation to lower the pH from 4.17 to 1.99. The extent of whiteness of the sample appeared to increase slightly, but overall the precipitate remained stable as the pH was lowered. Because the precipitate did not dissolve at low pH, the test showed that the zinc polyphosphate precipitate is acid resistant in the presence of the BSA protein.

Example 6

A clear mixture of $ZnCl_2$, SHMP and water from the same batch as Example 1 was freeze dried. A white powder resulted. The ability of the solution to be freeze dried into powder indicates that the complex can be used in both liquid and solid phase.

The above data from the examples indicates that the soluble zinc phosphate mixture can potentially be used in formulations for sensitive teeth. At a certain molar ratio (approximately 20P:1Zn), soluble zinc polyphosphate solution can be obtained. When this soluble solution is mixed with BSA protein, it quickly starts to precipitate and is ready to treat dentinal tubules. In addition, $Zn^{2+}$ will hydrolyze to amorphous zinc hydroxide at a pH of above 5.5, such as about 7.0 to about 7.4 to physically block the dentinal tubules. Increased precipitate may form at the higher pH range of 7.0 to 7.4 as compared with the lower pH range.

Other experiments using an organic zinc reagent and SHMP showed that when a mole ratio of P:Zn is 6.1 or more, such as about 15:1 to about 25:1 or about 20:1 to about 23:1, a soluble zinc polyphosphate complex is formed and the solution becomes clear.

In summary, the soluble zinc polyphosphate complex of the present disclosure can precipitate at high pH and/or in the presence of protein (e.g., such as found in saliva) and thus can be applied to occlude dentinal tubules to provide dentinal hypersensitivity relief. Further, BSA in the above experiments simulates sweat proteins. Based on the data, it is believed that the complexes of the present disclosure can diffuse into sweat glands and precipitate in combination with protein to block the sweat ducts of a user, thereby preventing or reducing the amount of sweat coming out of the skin when used as an active ingredient in antiperspirants. In essence, the solubility characteristics of the zinc complex allows it to readily diffuse into dentin tubules or sweat glands and precipitate, thereby blocking the tubules or glands. The solubility can also allow formulation into liquid products, such as mouthwash. Additionally, the soluble Zinc complex can potentially be used to make transparent products.

What is claimed is:

1. An oral care composition, comprising:
   a soluble zinc polyphosphate complex where the phosphorous to zinc mole ratio of the complex is 20:1, wherein the complex is made by combining zinc chloride and sodium hexametaphosphate and a solvent, wherein the solvent is water,
   wherein the zinc chloride and the sodium hexametaphosphate are in sufficient amounts to provide a 20:1 mole ratio of phosphorus to zinc in the recited complex;
   wherein when the soluble zinc polyphosphate complex is mixed with a protein a precipitate forms that can occlude dentinal tubules.

2. The oral care composition of claim 1, wherein the zinc polyphosphate complex has a property of becoming insoluble at a pH ranging from about 5.5 to about 6.5.

3. The oral care composition of claim 1, wherein the zinc polyphosphate complex is insoluble at a pH below 5.5 in the presence of salivary proteins.

* * * * *